United States Patent [19]

Shaltiel

[11] Patent Number: 5,491,129
[45] Date of Patent: Feb. 13, 1996

[54] SYNTHETIC PEPTIDES DERIVED FROM VITRONECTIN AND PHARMACEUTICAL COMPOSITIONS COMPRISING THEM

[75] Inventor: Shmuel Shaltiel, Rehovot, Israel

[73] Assignee: Yeda Research and Development Co. Ltd., Rehovot, Israel

[21] Appl. No.: 98,005

[22] Filed: Jul. 29, 1993

[30] Foreign Application Priority Data

Jul. 30, 1992 [IL] Israel ......................................... 102688
Dec. 31, 1992 [IL] Israel ......................................... 104296

[51] Int. Cl.$^6$ .......................... A61K 38/00; C07K 5/00; C07K 7/00; C07K 17/00
[52] U.S. Cl. ................. 514/12; 514/11; 514/13; 530/317; 530/324; 530/326
[58] Field of Search .................. 514/11–13; 530/317, 530/324, 326

[56] References Cited

FOREIGN PATENT DOCUMENTS 0454199  2/1992  Japan.

OTHER PUBLICATIONS

Reilly et al, Fibrinolysis vol. 6 pp. 167–171 & (Jul. 1992).
Jenne et al, Biochem. vol. 26 pp. 6735–6742 (1987).
Suzuki et al, EMBO J. vol. 4 pp. 2519–2524 (1985).
De Boer et al., *Binding of Vitronectin–Thrombin–Antithrombin III Complex to Human Endothelial Cells Is Mediated by the Heparin Binding Site of Vitronectin*, The Journal of Biological Chemistry, vol. 267, No. 4, pp. 2264–2268, 1992.
Cajot et al., *Plasminogen–Activator Inhibitor Type 1 Is A Potent Natural Inhibitor of Extracellular Matrix Degradation by Fibrosarcoma and Colon Carcinoma Cells*, Proc. Natl. Acad. Sci. USA, vol. 87, pp. 6939–6943, Sep. 1990.
Chain et al., *The Phosphorylation of the Two–Chain Form of Vitronectin by Protein Kinase A is Heparin Dependent*, FEBS, vol. 269 No. 1, pp. 221–225, Aug. 1990.
Chain, et al., *Endogenous Cleavage of the Arg–379–Ala–380 Bond in Vitronectin Results in a Distinct Conformational Change Which 'Buries' Ser–378, Its Site of Phosphorylation by Protein Kinase A*, Biochem. J., vol. 274, pp. 387–395, 1991.
Chain et al., *Plasmin Cleavage of Vitronectin*, FEBS, vol. 285, No. 2, pp. 251–256, Jul. 1991.
Chmielewska, et al., *Evidence For A Rapid Inhibitor To Tissue Plasminogen Activator In Plasma*, Thrombosis Research, vol. 31, pp. 427–436, 1983.
Collen et al., *Identification and Some Properties of a New Fast–Reacting Plasmin Inhibitor in Human Plasma*, Eur. J. Biochem., vol. 69, pp. 209–216, 1976.
Dalhback et al., *Characterization of Human S Protein, An Inhibitor of the Membrane Attack Complex of Complement. Demonstration of a Free Reactive Thiol Group*, Biochemistry, vol. 24, pp. 2368–2374, 1985.
Dano et al., *Plasminogen Activators, Tissue Degradation, and Cancer*, Advances in Cancer Research, vol. 44, pp. 139–166, 1985.

Declerck et al., *Purification and Characterization of a Plasminogen Activator Inhibitor 1 Binding Protein From Human Plasma*, The Journal of Biological Chemistry, vol. 263, No. 30, pp. 15454–15461, 25 Oct. 1988.
Jenne et al., *Molecular Cloning of S–Protein, A Link Between Complement, Coagulation and Cell–Substrate Adhesion*, The EMBO Journal, vol. 4, No. 12, pp. 3153–3157, 1985.
Katagiri et al., *Bovine Endothelial Cell Plasminogen Activator Inhibitor*, Eur. J. Biochem., vol. 176, pp. 81–87, 1988.
Korc–Grodzicki et al., *Platelet Stimulation Releases A cAMP–Dependent Protein Kinase That Specifically Phosphorylates A Plasma Protein*, Proc. Natl. Acad. Sci. USA, vo. 85, pp. 7541–7545, Oct. 1988.
Korc–Grodzicki et al., *Vitronectin Is Phosphorylated By a cAMP–Dependent Protein Kinase Released By Activation Of Human Platelets With Thrombin*, Biochemical and Biophysical Research Communications, vol. 157, No. 3, pp. 1131–1138, 30 Dec. 1988.
Korc–Grodzicki et al., *An Enzymatic Assay for Vitronectin Based on Its Selective Phophorylation by Protein Kinase A*, Analytical Biochemistry, vol. 188, pp. 288–294, 1990.
Kost et al., *Mapping of Binding Sites for Heparin, Plasminogen Activator Inhibitor–1, and Plasminogen to Vitronectin's Heparin–Binding Region Reveals a Novel Vitronectin–Dependent Feedback Mechanism for the Control of Plasmin Formation*, The Journal of Biological Chemistry, vol. 267, No. 17, pp. 12098–12105, 1992.
Mignatti et al., *In Vitro Angiogenesis on the Human Amniotic Membrane: Requirement for Basic Fibroblast Growth Factor—Induced Proteinases*, The Journal of Cell Biology, vol. 108, pp. 671–682, Feb. 1989.
Mimuro et al., *Purification of a Protein from Bovine Plasma That Binds to Type 1 Plasminogen Activator Inhibitor and Prevents Its Interaction with Extracellular Matrix*, The Journal of Biological Chemistry, vol. 264, No. 2, pp. 936–939, 15 Jan. 1989.
Pollanen et al., *Ultrasonic Localization of Plasma Membrane–Associated Urokinase–Type Plasminogen Activator at Focal Contacts*, The Journal of Cell Biology, vol. 106, pp. 87–95, Jan. 1988.

(List continued on next page.)

Primary Examiner—Jill Warden
Assistant Examiner—Sheela J. Huff
Attorney, Agent, or Firm—Browdy and Neimark

[57] ABSTRACT

The invention relates to synthetic peptides derived from the $K^{348}$-$A^{380}$ (8–40 of SEQ ID NO:1) sequence of the vitronectin molecule. The peptides modulate the biological activities of plasminogen activator inhibitor-1 (PAI-1) and are useful as active ingredients of pharmaceutical compositions for the treatment of disorders such as bleeding disorders, acute myocardial infarction, deep vein thrombosis, pulmonary embolism, disseminated intravascular coagulation, tumor cell invasion and metastasis, inflammation, liver diseases, bacterial blood infections, pregnancy toxicosis, and pathological conditions associated with the control of angiogenesis, or with nerve regeneration, or with excessive tPA-mediated proteolysis.

19 Claims, 8 Drawing Sheets

OTHER PUBLICATIONS

Preissner et al., *Structural Requirements for the Extracellular Interaction of Plasminogen Activator Inhibitor 1 with Endothelial Cell Matrix–Associated Vitronectin*, The Journal of Cell Biology, vol. 265, No. 30, pp. 18490–18498, 25 Oct. 1990.

Rylatt et al., *An Immunoassay For Human D Dimer Using Monoclonal Antibodies*, Thrombosis Research, vol. 31, pp. 767–778, 1983.

Salonen et al., *Interaction of Plasminogen Activator Inhibitor (PAI–1) with Vitronectin*, The Journal of Biological Chemistry, vol. 264, No. 11, pp. 6339–6343, 14 Apr. 1989.

Sprengers et al., *Plasminogen Activator Inhibitors*, Blood, vol. 69, No. 2, pp. 381–387, Feb. 1987.

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
( A ) LENGTH: 43 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

```
Ala  Pro  Arg  Pro  Ser  Leu  Ala  Lys  Lys  Gln  Arg  Phe  Arg  His  Arg  Asn
 1                    5                        10                           15

Arg  Lys  Gly  Tyr  Arg  Ser  Gln  Arg  Gly  His  Ser  Arg  Gly  Arg  Asn  Gln
               20                        25                           30

Asn  Ser  Arg  Arg  Pro  Ser  Arg  Ala  Thr  Trp  Leu
               35                        40
```

SYNTHETIC PEPTIDES DERIVED FROM VITRONECTIN AND PHARMACEUTICAL COMPOSITIONS COMPRISING THEM

FIELD AND BACKGROUND OF THE INVENTION

The present invention relates to pharmaceutical compositions comprising synthetic peptides derived from vitronectin capable of modulating the biological activities of plasminogen activator inhibitor-1 (PAI-1) and to some such novel synthetic peptides.

Hemostasis, the process whereby bleeding from an injured blood vessel is arrested, is characterized by the combined activity of vascular, platelet and plasma factors as well as counterbalancing mechanisms to limit the accumulation of platelets and fibrin to the area of vessel wall injury.

Blood coagulation reactions form a key element of the hemostatic seal-the fibrin clot. Spreading outward from and anchoring the platelet plugs, the fibrin clot adds bulk needed for the hemostatic seal.

Regulatory mechanisms normally exist to prevent the blood coagulation reactions, once activated, from proceeding unchecked to cause pathological conditions, such as local thrombosis or disseminated intravascular coagulation (DIC). These regulatory mechanisms include cellular clearance of activated clotting factors, particularly as blood flows through the liver, and mechanisms within the blood itself for neutralizing the activated enzymes and cofactors of blood coagulation.

The fibrinolytic system is activated following the deposition of fibrin. By dissolving fibrin, this system helps keep open the lumen of an injured blood vessel. A balanced deposition and lysis of fibrin maintains and remolds the hemostatic seal during the several days required for an injured vessel wall to be repaired.

When fibrinogen is converted to fibrin by thrombin, plasminogen, an inert plasma precursor of plasmin, is activated by its natural activators, e.g., tissue plasminogen activator (tPA), and converted to the powerful proteolytic enzyme, plasmin, which degrades fibrin into soluble fragments, referred to as fibrin degradation products, which are swept into the circulation.

Several factors operate to prevent excessive fibrinolysis, including increased affinity of plasminogen for binding to fibrin rather than to fibrinogen, and the increased ability of tissue plasminogen activator to activate plasminogen when it is bound to fibrin. A major inhibitor of fibrinolysis is plasminogen activator inhibitor-1 (PAI-1). Moreover, plasma contains a protease inhibitor called α2-antiplasmin that can rapidly inactivate plasmin escaping from a fibrin clot.

In order to stop plasmin action it is not sufficient only to inactivate the excess of already-formed plasmin by $\alpha_2$-antiplasmin (Collen, 1976). It is also necessary to arrest further production of plasmin from plasminogen. This is achieved through the inhibition of plasminogen activator(s) by PAI-1, which was shown to be bound to vitronectin (Loskutoff et al., 1988; Sprengers and Kluft, 1987) and thus to become stabilized in its active form both in circulating blood and in the extracellular matrix (ECM) (Declerck et al., 1988; Salonen et al., 1989; Mimuro and Loskutoff, 1989; Preissner et al., 1990).

Figure 1:
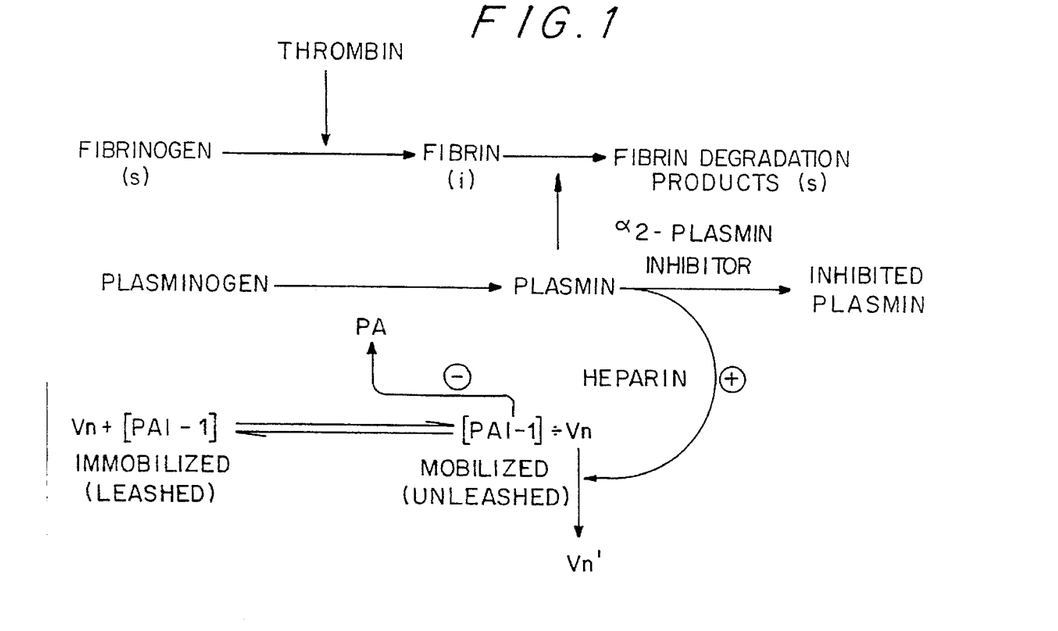
Figure 2:
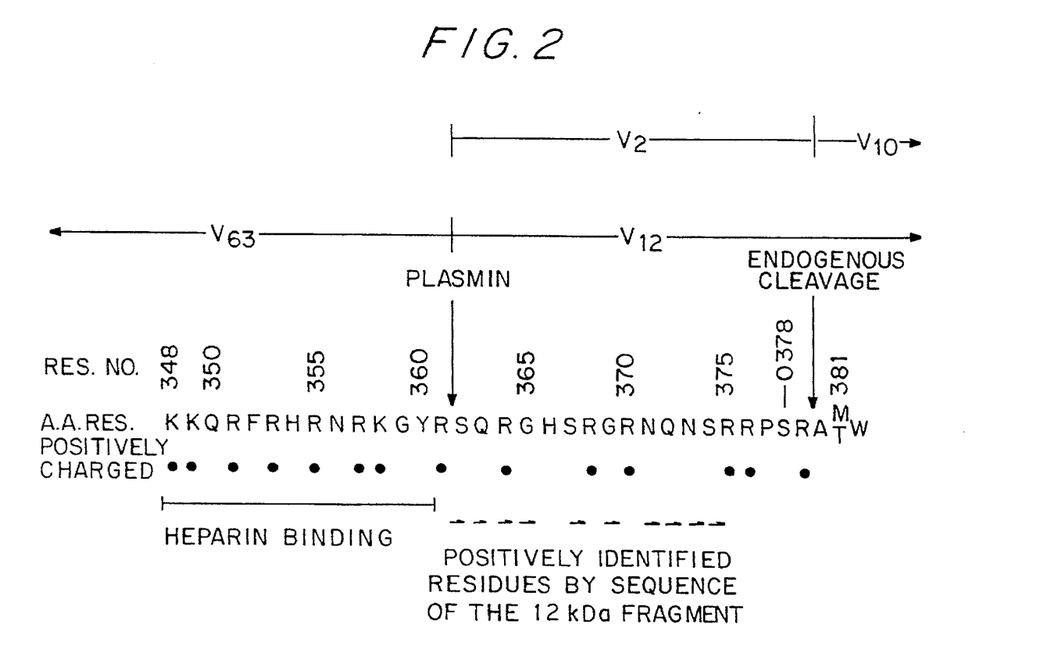

Originally discovered as a cell spreading factor, vitronectin is now recognized as a multifunctional regulatory protein involved in a variety of extracellular processes such as the attachment and spreading of normal and neoplastic cells, as well as the function of the complement and coagulation pathways. In circulating blood, vitronectin occurs in two molecular forms: a single chain 75 kDa polypeptide ($V_{75}$) and a nicked polypeptide ($V_{65+10}$) in which the two chains (65 kDa and 10 kDa) are linked by an interchain disulfide bridge. Using the specific phosphorylation of vitronectin at $Ser^{378}$ by platelet-released protein kinase A (PKA) (Korc-Grodzicki et al., 1988a; Korc-Grodzicki et al., 1988b; Chain et al., 1990; Korc-Grodzicki et al., 1990; Chain et al., 1991a), we recently showed (Chain et al., 1991b) that plasmin specifically cleaves vitronectin at the $Arg^{361}$-$Ser^{362}$ bond, 18 amino acids upstream from the site of the endogenous cleavage which gives rise to the two-chain form ($V_{65+10}$) of this protein. We also reported that as a result of the plasmin cleavage, the affinity between vitronectin and PAI-1 is significantly reduced (Chain et al., 1991b) and that this cleavage is stimulated by glycosaminoglycans which anchor vitronectin to the ECM, thus favouring the cleavage of the vitronectin molecules found in this matrix. On the basis of these findings, we proposed the mechanism depicted in FIG. 1, through which plasmin can arrest its own production by feedback signalling.

At the initial stage of fibrinolysis, the plasminogen activator converts plasminogen to plasmin. This is made possible since PAI-1 is then anchored (trapped) by the vitronectin molecules which were previously shown to be immobilized in the ECM (Pollanen et al., 1988), presumably through glycosaminoglycans. This anchoring of PAI-1 locally depletes the inhibitor by preventing it from reaching and inhibiting the plasminogen activator. When plasmin levels become too high, the excess plasmin can clip preferentially the vitronectin molecules immobilized in the subendothelium. Consequently, the equilibrium between anchored PAI-1 and the detached (mobile) PAI-1 is displaced, thus unleashing PAI-1 to be transferred to soluble (mobile) vitronectin molecules in plasma which can then reach and inhibit the plasminogen activator and arrest plasmin production. This unleashing actually represents a translocation, a transfer of the anchored PAI-1 from the ECM-bound (plasmin-clipped) vitronectin to the soluble vitronectin molecules which have not been clipped by plasmin and thus possess a higher affinity for PAI-1.

The impairment of this control mechanism of plasmin production may have wider clinical implications. Several findings suggest that the activation of plasminogen by its natural activators (e.g., tPA, streptokinase, urokinase) constitutes a multipurpose biological tool for the proteolytic dissolution of barriers by plasmin. In the case of blood clots, whether accidentally formed or no longer needed, their dissolution restores the free and vital flow of blood. However, the very same mechanisms is apparently exploited by malignant cells for penetrating tissues and forming metastases (Dano et al., 1985; Mignatti et al., 1989; Cajot et al., 1990), by nerve cells in nerve regeneration, and by blood vessels in angiogenesis (Mignatti et al., 1989). The plasminogen/plasmin system was also shown to be involved in inflammation, ovulation, tissue remodeling and development.

In view of this diversity of functions, it is obvious that plasmin activity must be under a strict regulatory control to secure a localized, site-restricted action and to limit its duration.

PAI-1 has an important role in the regulation of in plasminogen activation and as such, it is involved regulating the dissolution of biological barriers by plasmin. Consequently, through its functional interaction with PAI-1, vitronectin is involved in fibrinolysis, inflammation, ovulation, tissue remodeling and development, angiogenesis, nerve regeneration, malignancy and tumor cell invasion (Dano et al, 1985, Mignatti et al, 1989, Cajot et al, 1990).

Some peptides derived from the heparin binding site of vitronectin have been recently shown to mediate binding of vitronectin-thrombin-antithrombin III complex to human endothelial cells (de Boer et al, 1992). The peptides disclosed by de Boer correspond to sequences $A^{341}-R^{355}$ (1–15 of SEQ ID NO:1), $K^{348}-R^{361}$ (8–21 of SEQ ID NO:1), $R^{357}-R^{370}$ (17–30 of SEQ ID NO:1), $H^{366}-R^{379}$ (26–39 of SEQ ID NO:1), and $N^{371}-L^{383}$ (31–43 of SEQ ID NO:1). These same peptides were also used in a mapping study to localize the binding sites for heparin, PAI-1 and plasminogen in the carboxyl-terminal portion of vitronectin (Kost et al, 1992). None of these publications describe or suggest a pharmaceutical utility for these peptides.

SUMMARY OF THE INVENTION

It has now been found in accordance with the present invention that synthetic peptides derived from the vitronectin molecule can modulate the biological activities of PAI-1. Thus these peptides may either prevent PAI-1 from reaching and inhibiting plasminogen activator(s) or they may allow PAI-1 to reach and inhibit plasminogen activator(s).

The peptides of the invention, herein designated BP peptides, comprise amino acid sequences which correspond fully or partially to the cluster of basic amino acids corresponding to positions 348–380 (8–40 of SEQ ID NO:1) of the vitronectin molecule.

The present invention thus relates to pharmaceutical compositions comprising as active ingredients a synthetic peptide comprising a partial or full sequence including the amino acid residues $K^{348}-A^{380}$ (8–40 of SEQ ID NO:1) of vitronectin having the formula:

348
K K Q R F R H R N R K G Y R S Q R G H S R
380
G R N Q N S R R P S R A (8-40 of SEQ ID NO:1)

and salts, functional derivatives and analogs thereof, said analogs being obtained by one or more amino acid substitutions, additions or deletions, such that the overall nature of the peptide is conserved with regard to its high positive charge density and overall hydrophilic character, said peptides and salts, functional derivatives and analogs thereof being capable of modulating the biological activities of PAI-1, and a pharmaceutically acceptable carrier.

The invention further relates to a synthetic peptide comprising a partial or full sequence including the amino acid residues $K^{348}-A^{380}$ (8–40 of SEQ ID NO:1) of vitronectin and salts, functional derivatives and analogs thereof, as defined above, but excepting the peptides $A^{341}-R^{355}$ (1–15 of SEQ ID NO:1), $K_{348}-R^{361}$ (8–21 of SEQ ID NO:1), $R^{357}-R^{370}$ (17–30 of SEQ ID NO:1), $H^{366}-R^{379}$ (26–39 of SEQ ID NO:1) and $N^{371}-L^{383}$.

Illustrative examples of peptides according to the invention are shown in Schemes I and II herein. The numbering of the amino acid residues used herein refers to the vitronectin sequence deduced by Jenne and Stanley, 1985. The first sequence in Scheme I depicts the $K^{348}-W^{382}$ sequence of vitronectin (VN). The peptides may comprise all the optically active amino acids in L form or in D form or some of them will be in L and others in D form (amino acid residues in D form are underlined in Scheme II).

-continued
Scheme I

| | 348 | | | | | | | | | | | | | | 363 | |
|---|---|---|---|---|---|---|---|---|---|---|---|---|---|---|---|---|
| BP6 | K | K | Q | R | F | R | H | R | N | R | K | G | Y | R | S | Q (8–23 of SEQ ID NO: 1) |

SCHEME II

| | 348 … 363 |
|---|---|
| BP6 | K K Q R F R H R N R K G Y R S Q (8-23 of SEQ ID NO:1) |
| BP7 | $\underline{K}$ $\underline{K}$ Q $\underline{R}$ F $\underline{R}$ H $\underline{R}$ N $\underline{R}$ $\underline{K}$ G Y $\underline{R}$ S Q (8-23 of SEQ ID NO:1) |
| BP8 | $\underline{K}$ $\underline{K}$ $\underline{Q}$ $\underline{R}$ $\underline{F}$ $\underline{R}$ $\underline{H}$ $\underline{R}$ $\underline{N}$ $\underline{R}$ $\underline{K}$ G $\underline{Y}$ $\underline{R}$ $\underline{S}$ $\underline{Q}$ (8-23 of SEQ ID NO:1) |
| BP14 | $\underline{N}$ $\underline{R}$ $\underline{K}$ G $\underline{Y}$ $\underline{R}$ $\underline{S}$ $\underline{Q}$ (16-23 of SEQ ID NO:1) |

The peptides that prevent PAI-1 from reaching and inhibiting plasminogen activator(s) will enhance plasminogen activation to plasmin and consequent fibrinolysis. In this class are the peptides comprising fully or partially a sequence comprising the positions $K^{348}$-$R^{370}$ (8–30 of SEQ ID NO:1), most preferably $K^{348}$-$Q^{363}$ (8–23 of SEQ ID NO:1), of vitronectin, and they will be useful as profibrinolytic agents for the treatment of myocardial infarction, deep vein thrombosis, e.g., leg vein thrombosis, disseminated intravascular coagulation, pulmonary embolism and other disorders. They may be administered alone to enhance endogenous fibrinolytic processes, or in combined treatment with plasminogen activators, e.g. tPA, streptokinase or urokinase.

Thus, in one preferred embodiment, a peptide of the invention will comprise a sequence comprising fully or partially the positions $K^{348}$-$^{370}$ (8–30 of SEQ ID NO:1) of vitronectin, such as the peptides herein designated BP5 ($K^{358}$-$R^{370}$) (18–30 of SEQ ID NO:1) and BP6 ($K^{348}$-$Q^{363}$ (8–23 of SEQ ID NO:1)). Within this sequence, in a still further preferred embodiment, the peptide will comprise part of the optically active amino acid residues or, most preferably, all of them in the D configuration, such as the peptides herein designated BP7, BP8 and BP14. The peptide BP7 has the same sequence as BP6 ($K^{348}$-$Q^{363}$ (8–23 of SEQ ID NO:1)) but the underlined residues in Scheme II have D instead of L configuration. The peptide BP8 has the same sequence of BP6 but all the optically active amino acids have D configuration. The peptide BP14 ($N^{356}$-$Q^{363}$ (16–23 of SEQ ID NO:1)) contains the C-terminal moiety of BP8 and all its optically active amino acids have D configuration. Peptides that have some or all the optically active amino acids in D form will be much more or fully resistant to enzymatic cleavage by proteases that are involved in hemostasis and fibrinolysis.

The peptides that allow PAI-1 to reach and inhibit plasminogen activator(s) prevent formation of plasmin from plasminogen. In this class are the peptides comprising fully or partially a sequence comprising the positions $S^{362}$-$A^{380}$ (22–40 of SEQ ID NO:1) of vitronectin, and will be useful as antifibrinolytic agents for the treatment of disorders associated with excessive (uncontrolled) proteolysis by plasmin, as in bleeding disorders. An example of such antifibrinolytic agent is the peptide BP4.

Thus, in another preferred embodiment, a peptide of the invention comprises a sequence comprising fully or partially the positions $S^{362}$-$A^{380}$ (22–40 of SEQ ID NO:1) of vitronectin, such as the peptides herein designated BP4 ($S^{362}$-$A^{380}$ (22–40 of SEQ ID NO:1)), BP4-1 ($S^{362}$-$R^{370}$ (22–30 of SEQ ID NO:1)) and BP4-2 ($S^{362}$-$R^{368}$ (22–28 of SEQ ID NO:1)).

The peptides and pharmaceutical compositions of the invention will be useful to treat disorders in which modulation of PAI-1 is involved, e.g., myocardial infarction, deep vein thrombosis, e.g., leg vein thrombosis, pulmonary embolism, disseminated intravascular coagulation, tumor cell invasion and metastasis, inflammation, e.g., pancreatic inflammation, liver diseases, bacterial blood infections, pregnancy toxicosis, and pathological conditions associated with the control of angiogenesis, or with nerve regeneration, or with excessive tPA-mediated proteolysis, such as in metastasis.

BRIEF DESCRIPTION OF THE DRAWINGS

FIG. 1 is a scheme showing the sequence of molecular events involved in fibrinolysis, whereby plasmin can arrest its own production by feedback signaling, unleashing PAI-1 from the immobilized vitronectin found in the extracellular matrix (e.g. the vascular subendothelium), which becomes exposed at the locus of a hemostatic event. PA, plasminogen activator: PAI-1, plasminogen activator inhibitor-1; Vn, vitronectin; Vn', plasmin-clipped vitronectin; (s), soluble; (i) insoluble; +, stimulation; –, inhibition.

FIG. 2 is a scheme showing the sequence of a portion of vitronectin containing the positively charged cluster of basic amino acids (residues 348-380 (8–40 of SEQ ID NO:1)), and illustrating the relationship between the site of phosphorylation of PKA ($Ser^{378}$), the endogenous cleavage site ($Arg^{379}$-$Ala^{380}$ (39–40 of SEQ ID NO:1)), the plasmin cleavage site ($Arg^{361}$-$Ser^{362}$ (21–22 of SEQ ID NO:1)) and the heparin binding site (positions 348-359 (8–19 of SEQ ID NO:1)).

FIGS. 3A–D show the effect of synthetic peptides from the BP series corresponding to positions 348-380 (8–40 of SEQ ID NO:1) in vitronectin on the binding of vitronectin onto immobilized PAI-1. FIG. 3A -peptide BP1 (squares), BP2 (triangles) and no additions (circles); FIG. 3B-BP3 (squares), BP4 (triangles) and no additions (circles); FIG. 3C-BP(4-1) (squares), BP(4-2) (triangles) and no additions (circles); FIG.3D-BP(4-1) (squares), BP5 (triangles), BP6 (filled circles), and no additions (empty circles). Each point in the graph represents the mean of triplicate determinations. The final peptide concentrations in the incubation mixtures was 25 μM.

FIGS. 4A–B show the relative efficacy of equimolar concentrations (25 μM) of peptides BP4-1 (triangles) and BP5 (squares) (FIG. 4A) and peptides BP5 (filled circles) and BP6 (filled triangles) (FIG. 4B) in impeding the binding of vitronectin to immobilized PAI-1. No additions: empty circles.

FIG. 5A-2.5 µM (empty squares), 5 µM (empty triangles), 12 µM (filled circles), 25 µM BP4 (filled squares), no additions (empty circles); FIG. 5B-2.5 µM (empty squares), 10 µM (empty triangles), FIG. 5B-2.5 µM (filled circles), 100 µM (filled squares), 250 µM BP5 (filled triangles), no additions (empty circles); FIG. 5C-2.5 µM (empty squares), 5 µM (empty triangles), 10 µM (filled circles), 25 µM BP6 (filled squares), no additions (empty circles).

FIG. 8A-1 µM (empty squares), 5 µM (empty triangles), 10 µM BP7 (filled circles), no additions (empty circles); FIG. 8B-1 µM (empty squares), 5 µM (empty triangles), 10 µM BP8 (filled circles), no additions (empty circles); FIG. 8C-1 µM (empty squares), 5 µM (empty triangles), 10 µM BP14 (filled circles), no additions (empty circles).

FIG. 9 shows the profibrinolytic activity of the all-D peptide BP8. The enhancement of fibrinolysis was monitored by the measurement of fibrin clot lysis by D-dimer formation.

FIGS. 10A–E illustrate an experiment in which the profibrinolytic activity of BP8 was assessed in rats by the restoration of pulsatile blood pressure following administration of the drug at a dose of 50 µg/kg. FIG. 10A-control, animal with an unobstructed blood flow; FIG. 10B-animal with an obstructed blood flow; FIG. 10C-BP-8 treated animal, after 13 min; FIG. 10D-BP-8 treated animal, after 15 min; FIG. 10E-BP-8 treated animal, after 18 min.

DESCRIPTION OF PREFERRED EMBODIMENTS

The peptides of the invention have a high affinity for PAI-1 and are thus capable of displacing this inhibitor from vitronectin. They may unleash PAI-1 from the subendothelium or from the surface of aggregated platelets in an inhibitory form (bound to soluble vitronectin) and thus block plasmin formation and fibrinolysis, or unleash PAI-1 from vitronectin to allow its conversion into a latent (inactive) form and thus prevent the inhibition of plasminogen activators and promote fibrinolysis.

The efficacy of the peptides in the modulation of fibrinolysis may be assessed in vitro by methods such as fibrin D-dimer formation and release of PAI-1 by endothelial cells in culture, or in vivo by restoration of pulsatile blood flow in animals. Other commonly used clinical blood tests, including measurement of thrombin time, euglobulin lysis time, dilute whole blood clot lysis time, clot retraction, and release of tPA by endothelial cells in culture, may also be used.

As used herein, the term "salts" of the peptides and of functional derivatives and analogs thereof comprise salts of the free carboxylic groups of the amino acid residues with organic or inorganic bases as well as acid addition salts of free amino groups. The term "functional derivatives" consists of derivatives of free —OH, —NH$_2$— and —COOH groups, such as esters, e.g. phosphoric acid esters of S, T and Y residues, ethers, and amides, and the term "analogs" consists of peptides obtained by substitution, addition or deletion of amino acid moieties. The salts, functional derivatives and analogs of the peptides are encompassed by the invention as long as they are capable of modulating the biological activities of PAI-1.

The overall high positive charge density and hydrophilic character of the peptide should be conserved as required by the invention, and thus the amino acids to be added or used to substitute the residues in the vitronectin molecule should comply with this requirement. Negatively charged amino acids (E,D) and an excess of highly hydrophobic amino acids (W,F,Y,L,I) should be avoided. Positively charged amino acids (R, K, H) are recommended. Thus, for example, an interchange between R, K and H residues is possible.

The pharmaceutical composition of the invention comprises a peptide of the invention, a functional derivative, an analog or a salt thereof, and a pharmaceutically acceptable carrier. Any suitable mode of administration of the composition may be used, including oral, topical, by injection, or by intravenous infusion. It may be provided with various excipients, such as normal saline, glucose or other carriers, with or without additional therapeutic materials. Dosage rates will vary according to the condition of the patient and the particular treatment to be made. For example, lysis of clots can be effected in different body areas, including the brain, deep veins, coronary arteries and the like.

When the composition comprises the peptides that are profibrinolytic they may be administered alone or together with a plasminogen activator, such as natural or recombinant tissue plasminogen activator (tPA), urokinase or streptokinase.

The dosage forms for use in the invention are formulated using known pharmaceutical methods and procedures. They may be presented as powders or liquid suspensions.

The invention further relates to the use of a synthetic peptide comprising a partial or full sequence including the amino acid residues $K^{348}$-$A^{380}$ (8–40 of SEQ ID NO:1) of vitronectin and salts, functional derivatives and analogs thereof, said analogs being obtained by one or more amino acid substitutions, additions or deletions, such that the overall nature of the peptide is conserved with regard to its high positive charge density and overall hydrophylic character, said peptides and salts, functional derivatives and analogs thereof being capable of modulating the biological activities of PAI-1, for the preparation of pharmaceutical compositions for the treatment of various conditions, including acute myocardial infarction, deep vein thrombosis, pulmonary embolism, disseminated intravascular coagulation, tumor cell invasion and metastasis, inflammation, liver diseases, bacterial blood infections, pregnancy toxicosis and pathological conditions associated with the control of angiogenesis, or with nerve regeneration, or with excessive tPA-mediated proteolysis, e.g. metastasis.

In a further embodiment, the invention relates to a method of treatment of a patient afflicted with a disease selected from acute myocardial infarction, deep vein thrombosis, pulmonary embolism, disseminated intravascular coagulation, tumor cell invasion and metastasis, inflammation, liver diseases, bacterial blood infections, pregnancy toxicosis, and pathological conditions associated with the control of angiogenesis, or with nerve regeneration, or with excessive tPA-mediated proteolysis, said method of treatment comprising administering to such a patient a therapeutically effective amount of a peptide as defined herein as active ingredient of the pharmaceutical compositions of the invention.

The invention will now be illustrated by the following non-limiting examples.

EXAMPLES

Materials and Methods a) Materials purchased

Freshly-frozen human plasma was obtained from the Tel-Hashomer Medical Center, Ramat-Gan, Israel. Rabbit anti-human vitronectin polyclonal antibodies were obtained from Calbiochem. β-Galactosidase-linked Protein A and orthonitrophenyl-β-D-galactopyranoside (ONPG) were purchased from Amersham U.K. PAI-1 was obtained from American Diagnostica, New York. All other chemicals were of the best available grade from commercial sources.

b) Vitronectin

Vitronectin was prepared from freshly-frozen human plasma using a purification procedure described by Korc-Grodzicki et al., 1990. The preparations usually contained the two molecular forms of this protein: the one chain $V_{75}$ form and the proteolytically clipped, two chain $V_{65+10}$ form held together by a disulfide bridge (Dahlback and Podack, 1985; Jenne and Stanley, 1985).

c) Procedures carried out as described in the literature

Protein concentration was determined by the method described by Bradford, 1976. The binding of vitronectin to immobilized PAI-1 was conducted as described by Salonen et al., 1989. The activation of PAI-1 by sodium dodecylsulfate was carried out as described by Katagiri et al., 1988. Amino acid sequencing was performed with an Applied Biosystem 475A sequencer.

EXAMPLE 1

Synthesis of peptides

The peptides of the invention may be produced by chemical synthesis or by genetic engineering techniques using procedures well-known in the art.

The synthesis of peptides was carried out manually, in a mechanical shaker, using the solid phase methodology (Barany and Merrifield, 1980), on a chloromethylated polystyrene –1% divinylbenzene resin (Chemalog, South Plainfield, N.J.). α-Amino groups were protected by the t-butyloxycarbonyl (t-Boc) group. Side chain groups were masked by the following protecting groups: serine (S) and threonine (T), by benzyl; tyrosine (Y), by 2,6-dichlorobenzyl; lysine (K), by 2-chlorobenzyloxycarbonyl; arginine (R), by p-toluene-sulfonyl; and histidine (H), by benzyloxycarbonyl. The synthesis was initiated by coupling the C-terminal amino acid to the resin. Peptide elongation (coupling) was performed with a 3-fold molar excess of the protected amino acid and an equimolar mixture of N,N'-dicyclohexylcarbodiimide and 1-hydroxybenzotriazole as coupling agents. Deprotection and detachment of the peptides from the polymeric carrier was carried out with anhydrous HF. The crude peptides were purified to homogeneity by preparative HPLC (Lichrosorb RP-8; 7 μm; 250×10 mm; Merck, Darmstadt, Germany), employing a linear gradient established between 0.1% trifluoroacetic acid (TFA) in water and 0.1% TFA in 75% acetonitrile/water.

In order to map the PAI-1 binding site in vitronectin, a series of peptides was synthesized, the structure of which was derived from the amino acid sequence surrounding its plasmin cleavage site ($R^{361}$-$S^{362}$ (21–22 of SEQ ID NO:1)) (Chain et al., 1991b). The sequences of the peptides prepared are given in Schemes I and II hereinbefore. The structure of each of the peptides was confirmed by determination of its amino acid composition and sequence. The amino acid analysis of peptides BP4, BP4-1, BP5, BP6 and BP7 are presented in Table 1. The sequence analysis of peptides BP4, BP5 and BP6 are shown in Table 2.

TABLE 1

Amino Acid Composition of Key Peptides in the BP Series*

| Peptides | A | R | N | Q | G | H | K | F | P | S | Y |
|---|---|---|---|---|---|---|---|---|---|---|---|
| BP4 | 0.85 | 5.32 | 1.98 | 2.14 | 2.0 | 0.98 | — | — | 1.0 | 2.4 | — |
|  | (1) | (6) | (2) | (2) | (2) | (1) |  |  | (1) | (4) |  |
| BP4-1 | — | 2.95 | — | 1.06 | 2.0 | 1.12 | — | — | — | 1.32 | — |
|  |  | (3) |  | (1) | (2) | (1) |  |  |  | (2) |  |
| BP5 | — | 4.1 | — | 1.10 | 3.0 | 1.02 | 0.86 | — | — | 1.56 | 1.05 |
|  |  | (4) |  | (1) | (3) | (1) | (1) |  |  | (2) | (1) |
| BP6 | — | 5.0 | 1.02 | 2.18 | 1.0 | 0.97 | 3.38 | 0.90 | — | 0.81 | 1.10 |
|  |  | (5) | (1) | (2) | (1) | (1) | (3) | (1) |  | (1) | (1) |
| BP7 | — | 5.18 | 0.99 | 2.11 | 1.10 | 0.84 | 2.86 | 1.0 | — | 0.86 | 0.92 |
|  |  | (5) | (1) | (2) | (1) | (1) | (3) | (1) |  | (1) | (1) |

*Values given are the number of nanomoles obtained in the analysis, while the values in brackets represent the integer numbers expected for the correct structure.

TABLE 2

Sequence Analysis of BP4, BP5 and BP6

| BP4 | | | BP5 | | | BP6 | | |
|---|---|---|---|---|---|---|---|---|
| | Sequence determined | | | Sequence determined | | | Sequence determined | |
| Cycle No. | Residue | (yield*) | Cycle No. | Residue | (yield*) | Cycle No. | Residue | (yield*) |
| 1 | S | (58) | 1 | K | (64) | 1 | K | (62) |
| 2 | Q | (97) | 2 | G | (47) | 2 | K | (67) |
| 3 | R | ** | 3 | Y | (61) | 3 | Q | (68) |
| 4 | G | (48) | 4 | R | ** | 4 | R | (13) |
| 5 | H | (45) | 5 | S | (20) | 5 | F | (69) |
| 6 | S | (37) | 6 | Q | (44) | 6 | R | (19) |
| 7 | R | ** | 7 | R | ** | 7 | H | (14) |

TABLE 2-continued

Sequence Analysis of BP4, BP5 and BP6

| | BP4 | | | BP5 | | | BP6 | |
|---|---|---|---|---|---|---|---|---|
| | Sequence determined | | | Sequence determined | | | Sequence determined | |
| Cycle No. | Residue | (yield*) | Cycle No. | Residue | (yield*) | Cycle No. | Residue | (yield*) |
| 8 | G | (34) | 8 | G | (26) | 8 | R | (22) |
| 9 | R | ** | 9 | H | (16) | 9 | N | (52) |
| 10 | N | (28) | 10 | S | (8) | 10 | R | (24) |
| 11 | Q | (20) | 11 | R | ** | 11 | K | (40) |
| 12 | N | (15) | 12 | G | (16) | 12 | G | (34) |
| 13 | S | (15) | 13 | R | ** | 13 | Y | (44) |
| 14 | R | ** | | | | 14 | R | (24) |
| 15 | R | ** | | | | 15 | S | (13) |
| 16 | P | (25) | | | | 16 | Q | (17) |
| 17 | S | (9) | | | | | | |
| 18 | R | ** | | | | | | |
| 19 | A | (12) | | | | | | |

*Number of pmoles of amino acid phenylthiohydantoin in derivative recovered
**Qualitatively identified (yield too low for quantitative determination)

EXAMPLE 2

Effect of synthetic peptides of the BP series on the binding of vitronectin onto immobilized PAI-1

Each of the synthetic peptides shown in Scheme I and each of the peptides containing amino acids with a D configuration (BP7, BP8 and BP14) was tested by a competition ELISA assay for its ability to inhibit the binding of vitronectin to immobilized activated PAI-1. The first screening (FIGS. 3A–3D) was carried out with an identical molar concentration (25 μM) of the peptides. In view of a possible variability in such tests (mainly due to some variability in the activated PAI-1 coating of the plates), a control of vitronectin alone was run alongside in each plate for reference.

The various synthetic peptides (all 50 μM) were dissolved in 50 μl of a buffer composed of PBS, Tween 20 (0.01%), polyethylene-glycol (average M.W. 8 kDa) (4% w/v). Each of the samples was added to a microtiter well coated with SDS-activated PAI, prepared as described by Katagiri et al., 1988. After an incubation of 30 min at 22° C., aliquots (50 μl) of a vitronectin solution (at various concentrations) in the same buffer were added to each well. This was followed by an incubation for 2 hrs at 37° C. The amount of bound vitronectin was determined with specific rabbit anti-human Vn antibodies (1:1000 dilution), followed by a β-galactosidase-linked protein A and using o-nitrophenyl-β-D-galactopyranoside (ONPG) as a substrate. The enzymatic reaction was allowed to proceed and the absorbance at 405+490 nm was measured. The results are shown in FIG. 3. Each point in the graphs represents the mean of triplicate determinations. The final peptide concentrations in the incubation mixtures are 25 μM and the concentrations for vitronectin are indicated.

Figure 3A:
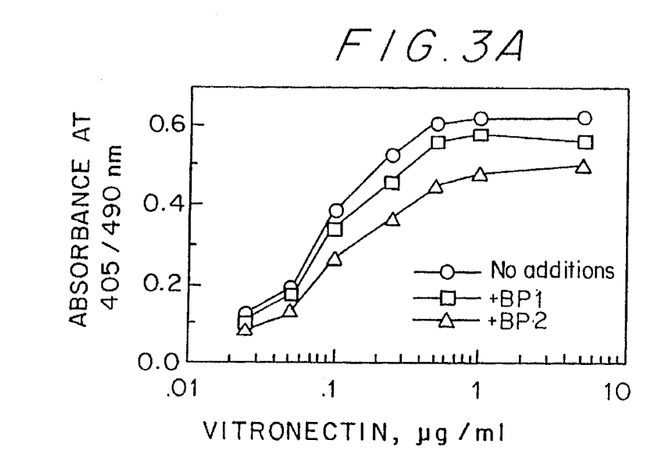
Figure 3B:
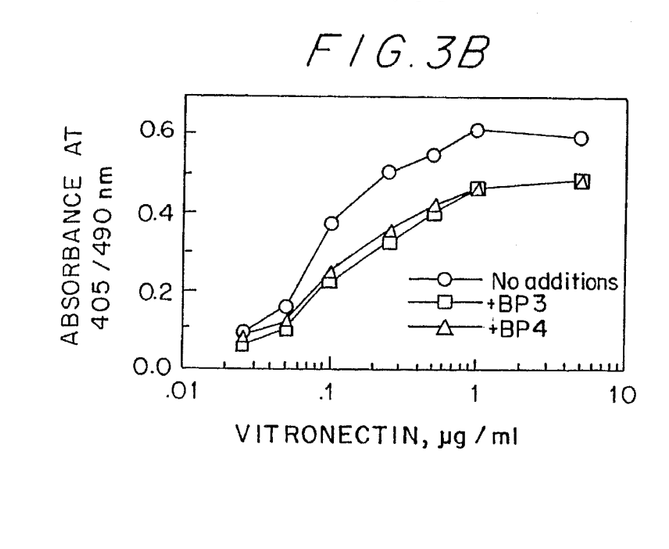
Figure 3C:
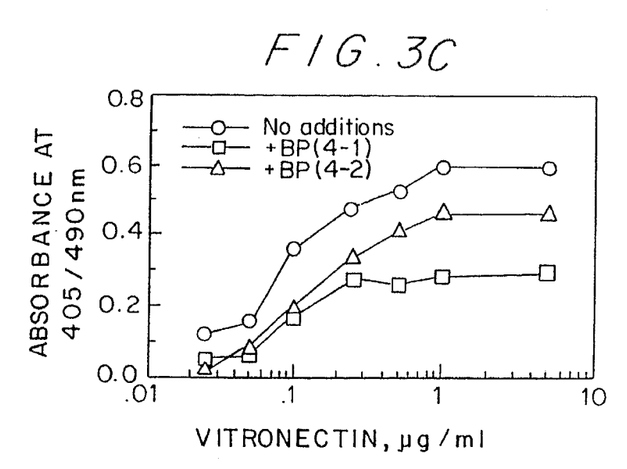

As seen in FIGS. 3A–D, all of the peptides BP1, BP2, BP3 and BP4 (FIGS. 3A and 3B) which cover the vitronectin sequence between the plasmin cleavage site ($R^{361}$-$S^{362}$ (21–22 of SEQ ID NO:1)) and the endogenous cleavage site ($R^{379}$-$A^{380}$ of SEQ ID NO:1)) inhibit to some extent the binding of vitronectin to PAI-1. This inhibition is mainly due to the N-terminus moiety of BP4, since BP4-1 ($S^{362}$-$R^{370}$ (22–30 of SEQ ID NO:1)) was a rather effective inhibitor (FIG. 3C, panel C) while BP1 ($N^{371}$-$A^{380}$ (31–40 of SEQ ID NO:1)) exhibited a very minor inhibition, if any (FIG. 3A, panel A). It should be noted that BP4-2 ($S^{362}$-$R^{368}$ (22–28 of SEQ ID NO:1)) which is only two amino acids shorter than BP4-1, was a less effective inhibitor (FIG. 3, panel C) suggesting that $G^{369}$ (29 of SEQ ID NO:1) and/or $R^{370}$ (30 of SEQ ID NO:1) may contain an important biorecognition element. Furthermore, the inhibition capacity of the various peptides could not be attributed merely to their positive charge, since BP4-1 (net charge +4) was found to be more effective than BP3 (net charge +6) or BP4 (net charge +7) (FIG. 3, panels B and C).

Figure 3D:
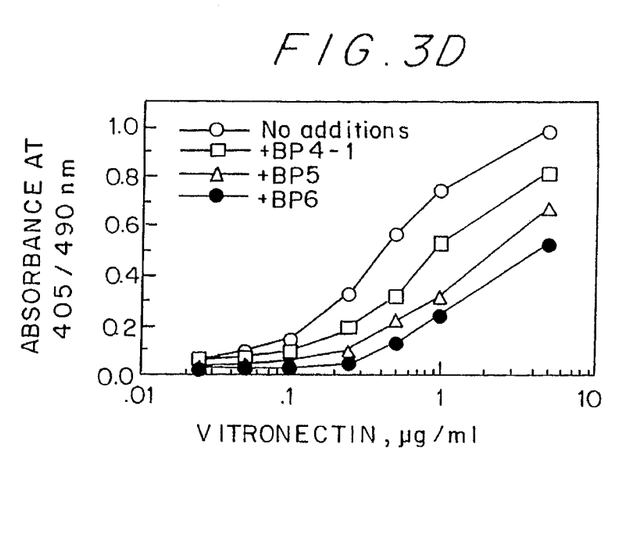

The peptide BP5 ($K^{358}$-$R^{370}$ (18–30 of SEQ ID NO:1)), which contains all of BP4-1 and a further extension beyond the plasmin cleavage site, was found to be more effective than BP4-1 as an inhibitor (FIG. 3D). Furthermore, the peptide BP6 ($K^{348}$-$Q^{363}$ (8–23 of SEQ ID NO:1)) seemed to be the most effective in this series FIG. 3D).

The relative inhibitory power of the peptides BP4, BP5 and BP6 was then assessed by measuring the concentration dependence of the inhibition.

Figure 4A:
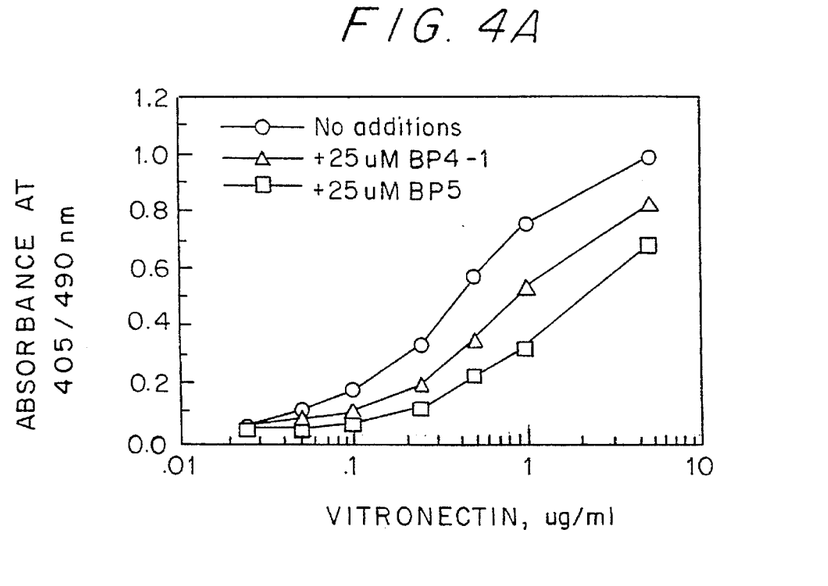
Figure 4B:
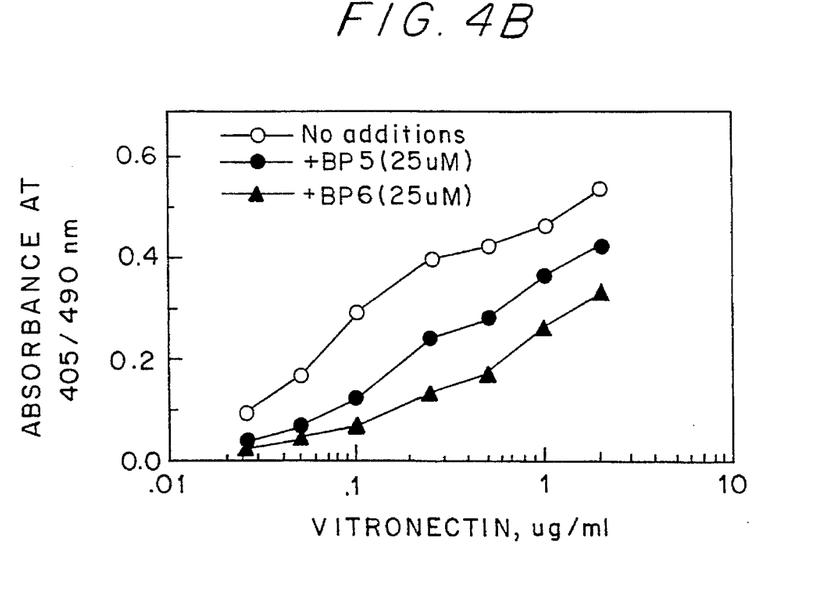

As shown in FIG. 4, on an equimolar basis (25 μM of each peptide), BP5 is superior to BP4-1 (panel A) and BP6 is more efficient than BP5 (panel B).

Figure 5A:
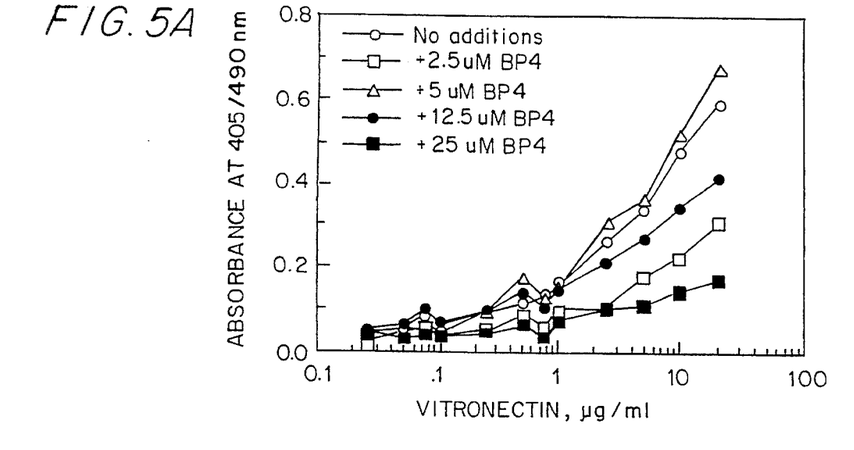
FIGS. 5A–C show the effect of different concentrations of BP4 (FIG. 5A), BP5 (FIG. 5B) and BP6 (FIG. 5C) on the binding of vitronectin to immobilized PAI-1.
Figure 5B:
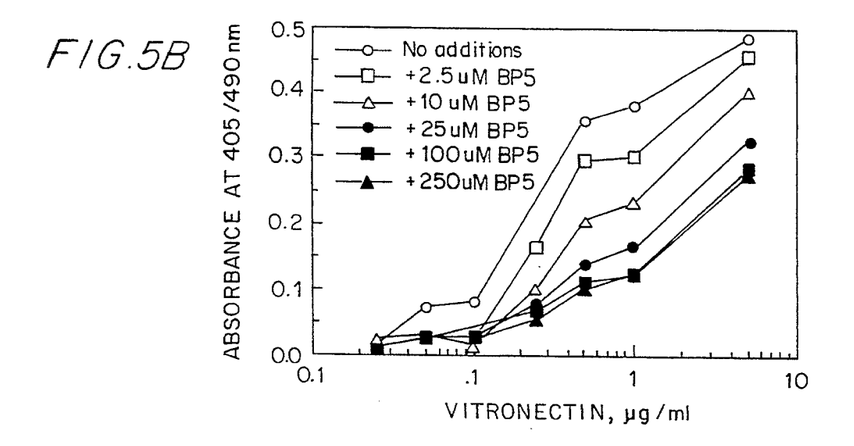
Figure 5C:
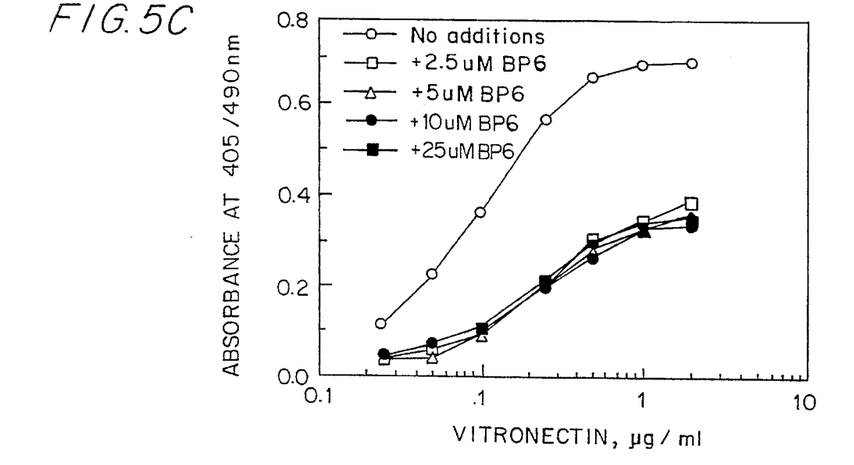

As seen in FIG. 5, all three of the peptides BP4, BP5 and BP6 achieved a maximal inhibition with increasing concentration. However, while BP4 did so at a concentration of 25 μM (FIG. 5A), and BP5 at a concentration of 100 μM (FIG. 5B), the peptide BP6 was maximally effective already at a 2.5 μM concentration (FIG. 5C).

Figure 6:
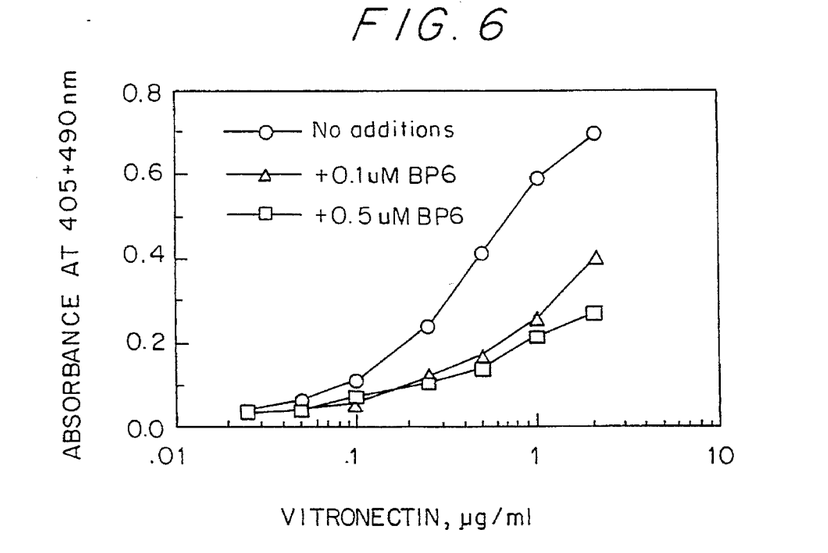
FIG. 6 shows the effect of small concentrations of BP6 on the binding of vitronectin to immobilized PAI-1. No additions: circles, 0.1 µM BP6 (triangles), 0.5 µM BP6 (squares).
Figure 7:
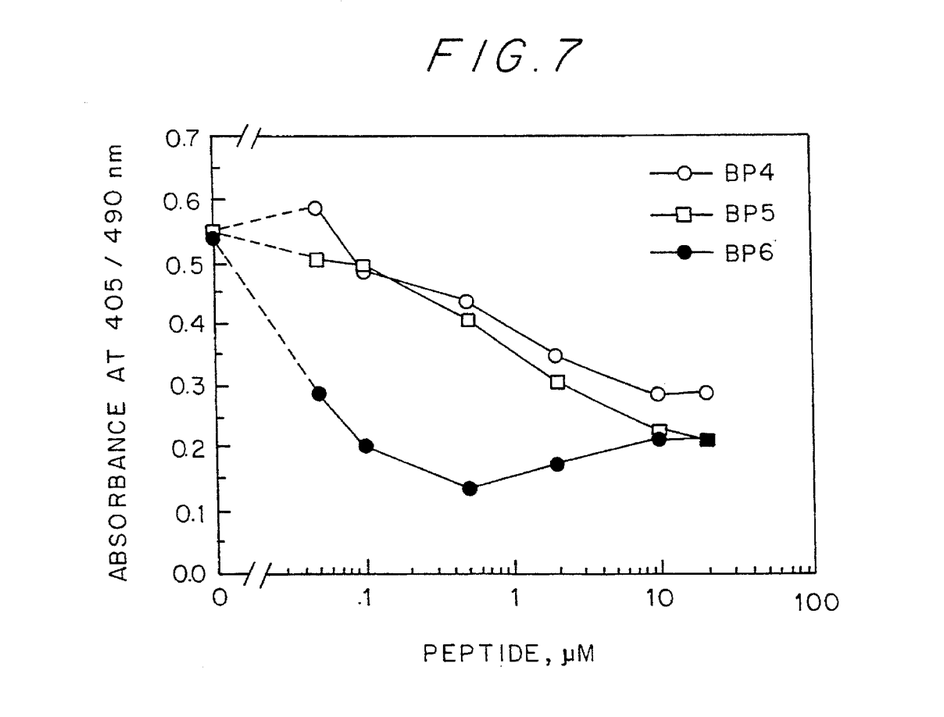
FIG. 7 illustrates the comparison of the efficacy of BP4 (empty circles), BP5 (empty squares) and BP6 (filled circles) in impeding the association of vitronectin to PAI-1. The final concentration of vitronectin was constant (0.5 µg/ml), while the concentration of the peptides was varied as indicated.

This is further illustrated in FIG. 6, where a maximal inhibition of PAI-1 binding was already achieved with a peptide BP6 concentration of 0.1 μM (0.15 μg/ml), and in FIG. 7 where the relative inhibitory efficacy of these peptides is compared at one concentration of vitronectin (0.5 μg/ml) and with increasing peptide concentrations. It is apparent from this figure that all three peptides achieve the same level of inhibition (approximately 65%). However, BP6 achieves this level of inhibition at a concentration which is 200–500 fold lower than BP4 and BP5.

The results presented above indicate that while some high affinity elements of the PAI-1 binding site reside within the $K^{348}$-$R^{357}$ (8–17 of SEQ ID NO:1) region, the complete PAI-1 binding site encompasses the $K^{348}$-$R^{370}$ (8–30 of SEQ ID NO:1)) sequence. This positioning of the PAI-1 binding site can account for our previous finding (Chain et al., 1991b) that upon cleavage of the $R^{361}$-$S^{362}$ (21–22 of SEQ ID NO:1) bond by plasmin, the affinity between vitronectin and PAI-1 is attenuated to unleash the inhibitor, since the PAI-1 binding site is split in two by this cleavage.

Figure 8A:
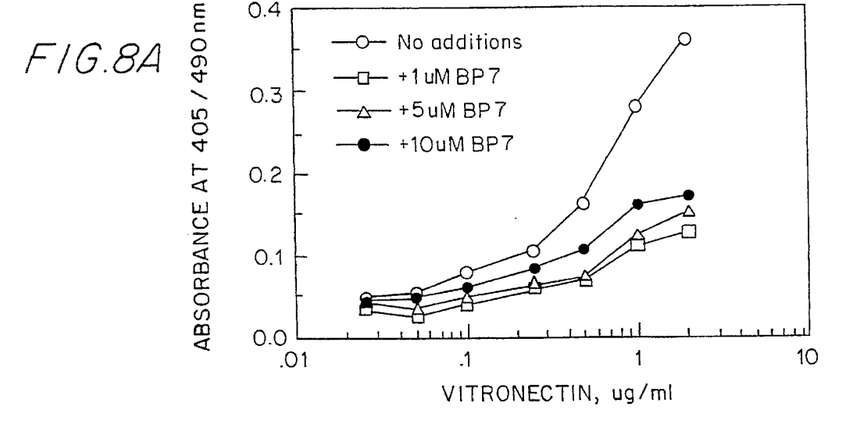
FIGS. 8A–C show the effect of different concentrations of the peptides BP7 (FIG. 8A), BP8 (FIG. 8B) and BP14 (FIG. 8C), comprising amino acids with D configuration on the binding of vitronectin onto immobilized PAI-1.
Figure 8B:
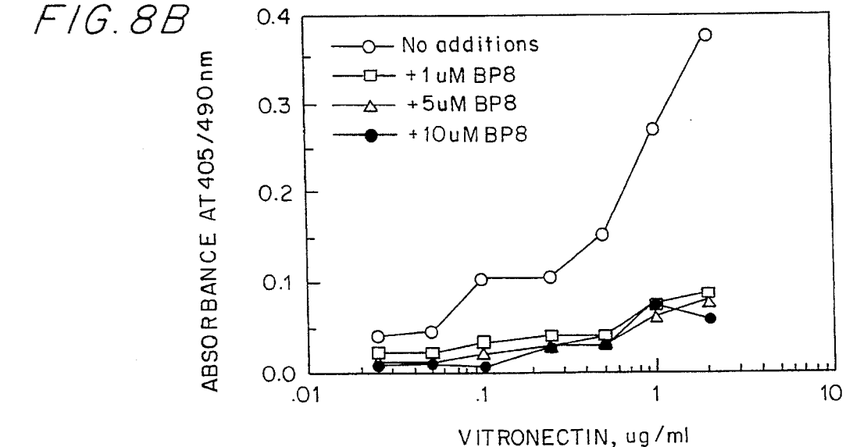
Figure 8C:
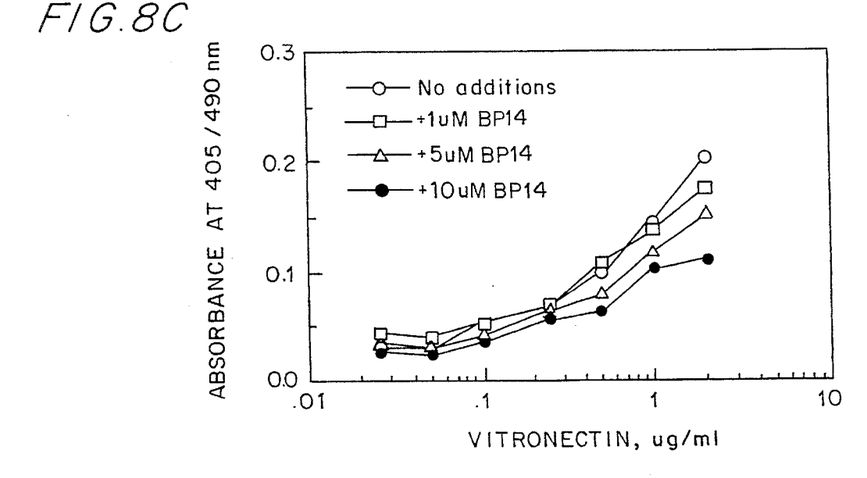

With regard to the peptides containing amino acids having D configuration, FIGS. 8A–C show that all three peptides BP7 (FIG. 8A), BP8 (FIG. 8B) and BP14 (FIG. 8C) bind to immobilized PAI-1, but BP8 seems to bind more strongly than BP7 and BP14.

EXAMPLE 3

Effect of synthetic peptides of the BP series on modulation of fibrinolysis

The efficacy of the synthetic peptides of the invention in the modulation of fibrinolysis is assessed by commonly used clinical blood tests, mainly modulation of fibrin clot lysis with fibrin D-dimer formation and release of PAI-1 by endothelial cells in culture. Other tests that may be used include measurements of thrombin time, euglobulin lysis time, dilute whole blood clot lysis time, clot retraction, and release of tPA by endothelial cells in culture.

3.1 Modulation of fibrin clot lysis by D-dimer formation

For the assessment of the ability of the peptides to modulate fibrin clot lysis in the absence or in the presence of added tPA, a fibrin clot gel was formed on human endothelial cells (from a human umbilical cord) seeded in a dense layer, using human fibrinogen (which contains some plasminogen) and thrombin. Thus, human endothelial cells (HUVEC) were cultured in semiconfluent way on 24 wells tissue culture plate, precoated or not with extracellular matrix. The cells were washed and 0.4 ml fibrin gel which was constructed by mixing 3 mg/ml human fibrinogen and 1 unit thrombin (Kabi, Sweden), was overlayed on the cells. The fibrin was allowed to clot for 1 hour at 37° C. and 0.4 ml medium (M-199 with 10% fetal calf serum (FCS)) containing the peptide to be tested was put on the fibrin gel. tPA with or without the assayed substances were diluted in the supernatant and incubated with the cells for 6 hours. Samples from the supernatant were tested in the D-Dimer EIA. Presence of D-dimer in the supernatant was assayed by enzyme immunoassay according to Rylatt et al., 1983, using a kit from Agen Biomedical Ltd., Brisbane, Australia. D-Dimer formation was determined in the supernatants of 2 wells after 6 hours of incubation with the peptide to be tested, and in the absence or presence of tPA (0.09 U/ml). The different peptide solutions were added to the fibrin gel 1 hour after clotting. In the absence of added peptides and under the conditions used, such clots are lysed in about 24 hours, due to the activation of plasminogen by the tPA which is released from the cells. Exogenous tPA may be added to accelerate the process and simulate a tPA treatment. The results are shown in Table 3.

TABLE 3

Biological activity of the peptides, measured by their ability to modulate fibrin clot lysis

| Peptide | Final Concentration (M) | Presence of added tPA | Clot lysis measured by D-dimer formation (%)* (mean) |
|---|---|---|---|
| BP4 | $1.5 \times 10^{-9}$ | + | 76 |
|  | $4.5 \times 10^{-9}$ | + | 57 |
|  | $1.5 \times 10^{-8}$ | + | 48 |
|  | $4.5 \times 10^{-6}$ | + | 60 |
| BP5 | $4.5 \times 10^{-9}$ | + | 183 |
|  | $1.5 \times 10^{-8}$ | + | 174 |
|  | $4.5 \times 10^{-7}$ | + | 144 |
|  | $4.5 \times 10^{-6}$ | + | 132 |
| BP5 | $1 \times 10^{-8}$ | − | 183 |
|  | $1 \times 10^{-6}$ | − | 191 |
| BP6 | $1 \times 10^{-6}$ | + | 121 |

TABLE 3-continued

Biological activity of the peptides, measured by their ability to modulate fibrin clot lysis

| Peptide | Final Concentration (M) | Presence of added tPA | Clot lysis measured by D-dimer formation (%)* (mean) |
|---|---|---|---|
| BP6 | $1 \times 10^{-9}$ | − | 152 |
|  | $1 \times 10^{-8}$ | − | 135 |
|  | $1 \times 10^{-6}$ | − | 187 |

*Control is taken as 100%. Therefore, values above 100% indicate enhanced fibrinolysis while values below 100% indicate diminished fibrinolysis.

Profibrinolytic peptides, with values above 100%, e.g., BP5 and BP6, accelerate the process, while anti-fibrinolytic peptides, with values below 100%, e.g., BP4, will inhibit it. Among the peptides mentioned above, BP6 is the most efficient profibrinolytic peptide tested as can be seen from another series of experiments carried out with BP6 at different concentrations. The results are summarized in Table 4.

TABLE 4

Biological activity of peptide BP6 measured by its ability to modulate fibrin clot lysis

| BP6 Final Concentration (M) | Clot lysis measured by D-dimer formation (%)* (mean) | number of experiments |
|---|---|---|
| $1 \times 10^{-5}$ | 145 | 4 |
| $1 \times 10^{-6}$ | 162 | 4 |
| $3.3 \times 10^{-7}$ | 163 | 4 |
| $1 \times 10^{-7}$ | 120 | 8 |
| $3.3 \times 10^{-8}$ | 147 | 4 |
| $1 \times 10^{-8}$ | 168 | 2 |
| $3.3 \times 10^{-9}$ | 125 | 2 |

*Control is taken as 100%. Values above 100% indicate enhanced fibrinolysis.

The results are in accordance with the relative capacity of BP6 vis-a-vis the other peptides in impeding the binding of vitronectin onto immobilized PAI-1, as shown in FIGS. 3A–3D to 7 herein.

Figure 9:
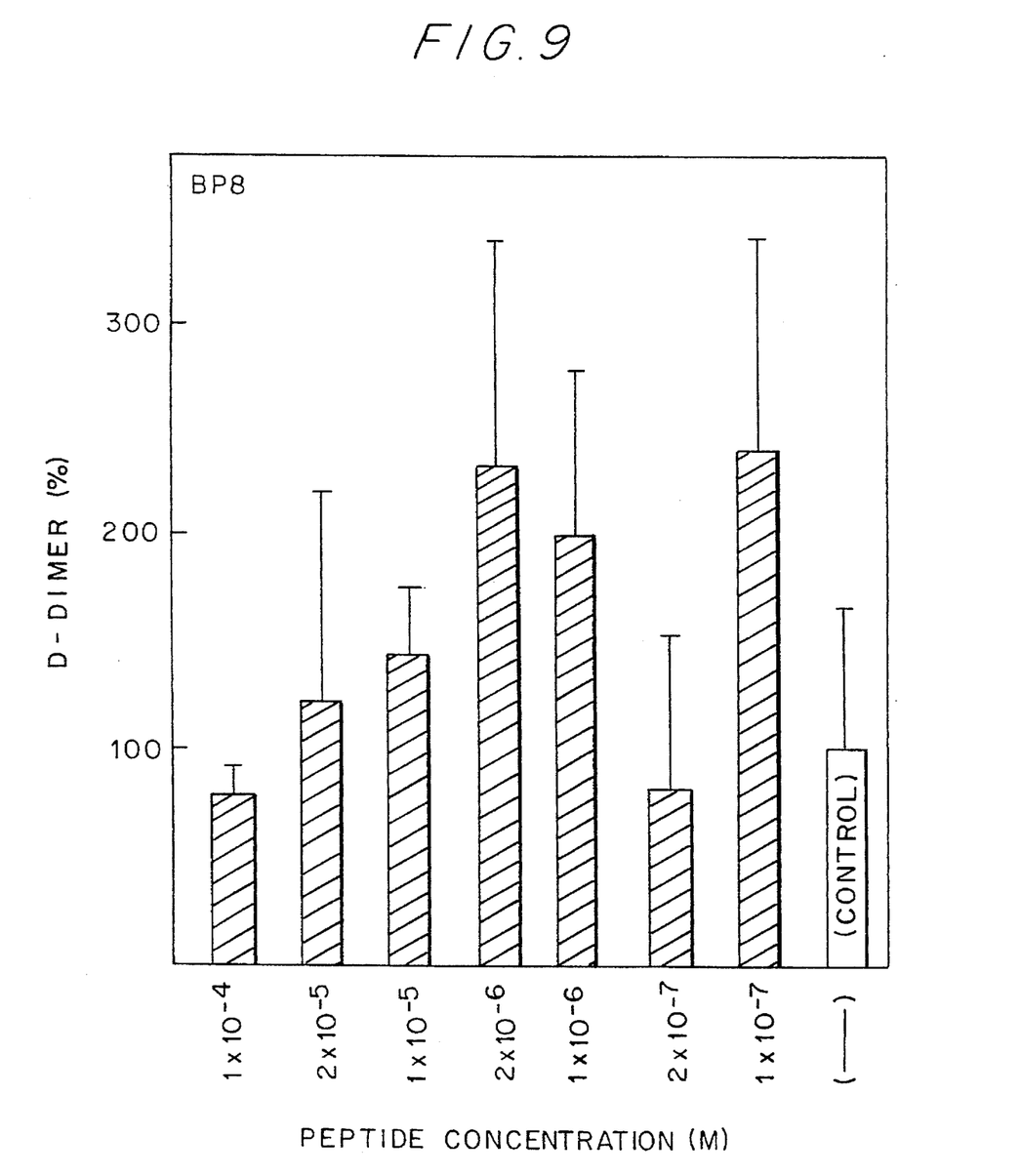

In a further experiment, the profibrinolytic activity of the all-D peptide BP8 ($K^{348}$-$Q^{363}$ (8–23 of SEQ ID NO:1)) was assayed. These assays were performed in hexaplicates with the same plasma pool (from healthy donors). The citrated plasma (200 µl) was overlayered on the human endothelial cells and was coagulated with 1 U/ml thrombin. The tested substances were diluted in 250 µl HBSS (Hank's Balanced Salt Solution) with 1% FCS and overlayered on the plasma clots. Samples for D-dimer analysis were taken after 6 hours. As shown in FIG. 9, BP8 significantly enhances fibrinolysis up to 2.5 fold in comparison to control (extreme right, no peptide added).

3.2 Effect on fibrinolysis in vivo in animals

The effect of the peptides on the fibrinolysis in vivo is evaluated in animals, e.g., rats, rabbits, guinea pigs, which are injected with the tested peptides. The experimental system includes the measurement of plasminogen, α-2 antiplasmin and D-dimer with or without the addition of tPA in the tested plasma. In this system, tPA may be injected with the peptides to determine their additional modulatory effect on fibrinolysis.

The profibrinolytic effect of BP8 in rats was assessed using the following experimental procedure.

3.2.a Animals. Male Wistar SPF rats were purchased from Harlan Olac, U.K. and allowed to acclimatize to the animal house at the Sackler School of Medicine, Tel-Aviv, Israel.

The animals used were mature rats aged 5–6 months and weighed from 400–500 grams.

3.2.b Animal Preparation. Blood pressure and heart rate were measured in conscious rats. The animals were lightly anesthetized with Avertin (2,2,2-tribromoethanol in 2-methyl-2-butanol diluted in saline) and chronic in-dwelling catheters were implanted in the caudal artery, for blood pressure measurement and in the jugular vein, for intravenous drug administration. The animals were allowed to recover from the surgery and anesthesia and were tested at least 24 hrs after implantation. The catheters were implanted so that blood pressure could be measured in the rat's home cage without any further handling or manipulation. To prevent clotting overnight, the catheters were filled with heparinized saline (500 units/ml) and during the test period, flushed with heparinized saline (50 units/ml).

3.2.c Blood Pressure and Heart Rate Recording and Data Analysis. The arterial catheter was connected to a Statham pressure transducer and blood pressure was recorded on a Grass multichannel polygraph. The signal recorded on the polygraph was sampled and analyzed using an IBM compatible PC and digitalized using a DAS 8 A/D converter. Data processing was by sampling at a frequency of 250Hz for 10 seconds. The signal was analyzed by peak detection. This program extracted systolic, diastolic and mean blood pressure, as well as heart rate at pre-designated time intervals.

3.2.d Drug Administration. The fibrinolytic peptide BP8 was injected, when the arterial catheter was clogged, 3–4 days after surgery, in spite of the heparin administration. In these rats, saline could be injected via the arterial catheter, but blood could not be drawn and there was no pulsation and recording of blood pressure. The efficacy of the drug was assessed by its ability to restore the pulsatile blood pressure recording and the ease of drawing blood from the arterial catheter. The drugs were administered intra-arterially into the arterial catheter at a concentration of 50 µg/kg.

Figure 10A:
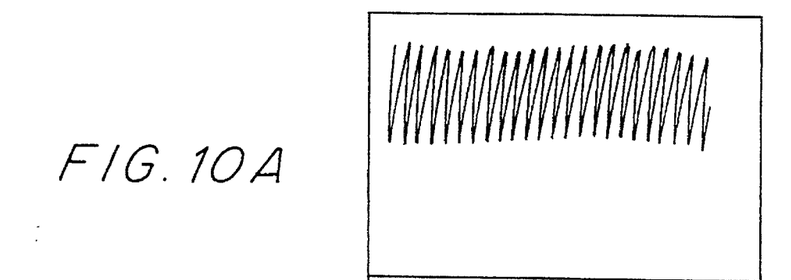
Figure 10B:
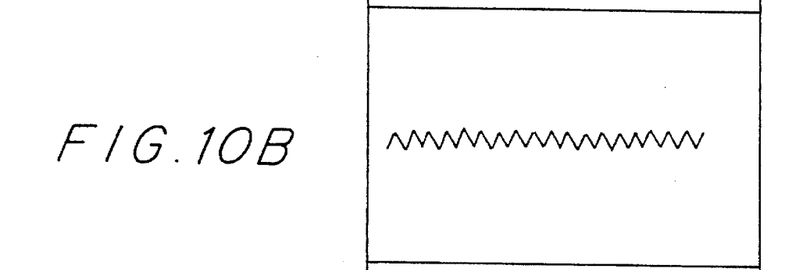
Figure 10C:
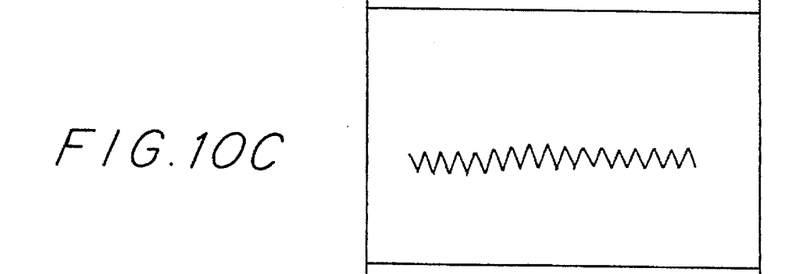
Figure 10D:
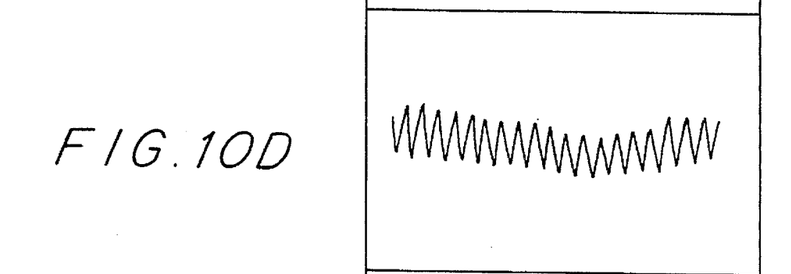
Figure 10E:
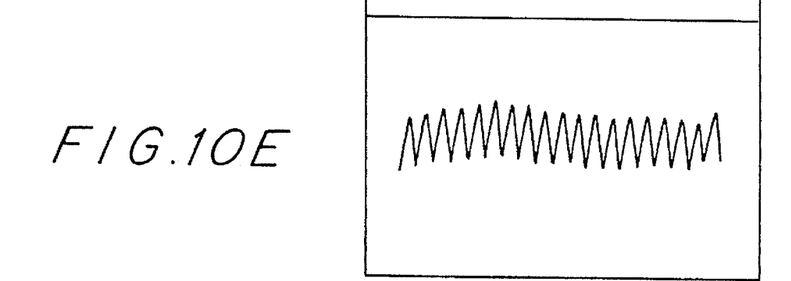

An example of such results is shown in FIGS. 10A–E wherein FIG. 10A and FIG. 10B depict, respectively, the pulsatile blood pressure of a healthy rat (control, unobstructed blood flow) and of a rat with an obstructed blood flow. After treatment of the latter with BP8, it is shown (FIG. 10E) that the pulsatile blood pressure is restored significantly after 18 minutes.

3.3 Release of PAI-1 by endothelial cells in culture

PAI-1 is determined in the supernatant of HUVEC cells according to the method of Chmielewska et al., 1983. Briefly, cells are cultured in semiconfluent way with or without ECM. The culture medium is changed for Hank's balanced salt solution with 2% FCS and the tested substances with or without added plasmin (5 µg/ml) are diluted in this buffer and incubated with the cells for 6 hours. Samples from the cell supernatant are assayed for the PAI-1 activity.

For the PAI-1 assay, the cell supernatant is incubated with a fixed amount of tPA (40 U/ml) and the residual activity of the tPA is determined by a substrate composed of plasminogen (0.1µg/ml), chromogenic substrate (S-2251) and stimulator (Kabi, Sweden). After incubation with the substrate, O.D. is measured at 405 nm and the amount of the inhibitor is calculated from calibration curve. PAI-1 antigen may also be determined with commercial kits.

The assay was carried out with BP6 and BP4 at various concentrations. The results are summarized in Tables 5 and 6.

TABLE 5

Effect of BP6 on the PAI-1 activity as measured in a model human endothelial cell system

| BP6 Final Concentration (M) | PAI activity % below control* (mean) | number of experiments |
|---|---|---|
| $1 \times 10^{-5}$ | 19.5 | 8 |
| $1 \times 10^{-6}$ | 36.5 | 8 |
| $3.3 \times 10^{-7}$ | 39 | 5 |
| $1 \times 10^{-7}$ | 19 | 2 |
| $1 \times 10^{-8}$ | 19 | 2 |

*Control taken as 100%.

TABLE 6

Effect of BP4 on the PAI-1 activity as measured in a model human endothelial cell system

| BP4 Final Concentration (M) | PAI activity % above control* (mean) | number of experiments |
|---|---|---|
| $1 \times 10^{-5}$ | 29 | 3 |
| $1 \times 10^{-6}$ | 47 | 3 |
| $3.3 \times 10^{-7}$ | 17 | 3 |
| $1 \times 10^{-7}$ | 0 | 2 |

*Control taken as 100%.

The profibrinolytic effect of BP6 (Table 5) is expressed through its ability to decrease the activity of PAI-1 in human endothelial cell system, thus increasing the activity of the plasminogen activator (tPA) and resulting in an increase in the plasmin activity and accelerated fibrinolysis, while the antifibrinolytic effect of BP4 (Table 6) is expressed through its ability to increase the activity of PAI-1 in the same system, thus decreasing the activity of the plasminogen activator (tPA) and resulting in a decrease in the plasmin activity and decelerated fibrinolysis.

3.4 Euglobulin Lysis Time

Citrated plasma is diluted in acetic acid (0.016M) in the cold and after 10 min. the precipitate is separated by centrifugation, dissolved in a borate buffer and allowed to clot by recalcification with $CaCl_2$ (0.025M). The clot incubated at 37° C. Normal clot lysis occurs between 2–3 hours. The tested substances are added to the plasma before the precipitation steps.

3.5 Dilute whole blood clot lysis time 1 ml of blood is diluted 1:10 in veronal buffer. A thrombus is formed by the addition of 100 µl of incubated thrombin (40 U/ml). The clotted blood is incubated at 37° C. for 48 hours. Normal clots will dissolve or may still be present after 48 hours. The addition of a pro-fibrinolytic agent will shorten the clot dissolution time.

REFERENCES

Barany, G. and Merrifield, R. B., in The Peptides: Analysis, Synthesis, Biology (Gross, E. and Meinhofer, J. eds.), Vol. 2, pp. 1–284 (Academic Press, New York) 1980 de Boer, H. C. et al, J. Biol. Chem. 267:2264–2268 (1992)

Bradford, M. M., Anal. Biochem. 72:248–254 (1976)

Cajot, J. F. et al., Proc. Natl. Acad. Sci. USA 87:6939–6943 (1990)

Chain, D. et al., FEBS Lett. 269:221–225 (1990)

Chain, D. et al., Biochem. J. 274:387–394 (1991a)

Chain, D. et al., FEBS Lett. 285:251–256 (1991b)

Chmielewska, J. et al., Thromb. Res. 31:427–436 (1983)

Collen, D., Eur. J. Biochem. 69:209–216 (1976)

Dahlback, B. and Podack, E. R. Biochemistry 24:2368–2374 (1985)
Dano, K. et al., Adv. Cancer Res. 44:139–166 (1985)
Declerck, P. J. et al., J. Biol. Chem. 263:15454–15461 (1988)
Jenne, D. and Stanley, K. K. EMBO J. 4:3153–3157 (1985)
Katagiri, K. et al., Eur. J. Biochem. 176:81–87 (1988)
Korc-Grodzicki, B. et al., Proc. Natl. Acad. Sci. USA 85:7541–7545 (1988a)
Korc-Grodzicki, B. et al., Biochem. Biophys. Res. Commun. 157:1131–1138 (1988b)
Korc-Grodzicki, B. et al., Anal. Biochem. 188:288–294 (1990)
Kost, C. et al., J Biol. Chem. 267:12098–12105 (1992)
Loskutoff, D. J. et al., in Progress in Thrombosis and Hemostasis (Coller, B. ed.), Saunders, Philadelphia, Vol. 9, pp. 87–115 (1988)
Mignatti, P. et al., J. Cell Biol. 108:671–682 (1989)
Mimuro, J. and Loskutoff, D. J., J. Biol. Chem. 264:936–939 (1989)
Pollanen, J. et al., J. Cell Biol. 106:87–95 (1988)
Preissner, K. T. et al., J. Biol. Chem. 265:18490–18498 (1990)
Rylatt et al., Thromb. Res. 31:767–778 (1983)
Salonen, E.-M. et al., J. Biol. Chem. 264:6339–6343 (1989)
Sprengers, E. D. and Kluft, C. Blood 69:381–387 (1987)

2. A molecule according to claim 1 wherein all amino acid residues have the L configuration.

3. A molecule according to claim 1, wherein said amino acid sequence consists of residues 18–30 of SEQ ID NO:1.

4. A molecule according to claim 1, wherein said amino acid sequence consists of residues 8–23 of SEQ ID NO:1.

5. A molecule according to claim 1, wherein at least one of the amino acid residues has the D configuration.

6. A peptide according to claim 5, wherein said amino acid sequence consists of the sequence:

Lys-Lys-Gln-Arg-Phe-Arg-His-Arg-Asn-Arg-Lys-Gly-Tyr-Arg-Ser-Gln (8–23 of SEQ ID NO:1), wherein the underlined amino acids have the D configuration.

7. A molecule according to claim 1 wherein all optically active amino acids have the D configuration.

8. A molecule according to claim 7, wherein said amino acid sequence consists of residues 8–23 of SEQ ID NO:1.

9. A molecule according to claim 7, wherein said amino acid sequence consists of residues 16–23 of SEQ ID NO:1.

10. A pharmaceutical composition comprising an effective amount of a molecule in accordance with claim 1 and a pharmaceutically acceptable carrier.

11. A method of treating an animal in need of increased fibrinolysis, comprising administering an effective amount of a molecule capable of inhibiting a biological activity of plasminogen activator inhibitor-1 (PAI-1) consisting of a

---

I claim:

1. A molecule capable of inhibiting a biological activity of plasminogen activator inhibitor-1 (PAI-1) consisting of a peptide having 8 to 23 consecutive amino acids of the sequence    Lys-Lys-Glu-Arg-Phe-Arg-His-Arg-Asn-Arg-Lys-Gly-Tyr-Arg-Ser-Gln-Arg-Gly-His-Ser-Arg-Gly-Arg (8–30 of SEQ ID NO:1), or a salt, functional derivative or analog thereof, said analog being obtained by one or more amino acid substitutions, additions or deletions such that the overall properties of the analog are conserved with regard to the overall positive charge density and overall hydrophilic character of the peptide, wherein said molecule does not include the peptides of residues 8–21 of SEQ ID NO:1 or 17–30 of SEQ ID NO:1.

peptide having 8 to 23 consecutive amino acids of the sequence    Lys-Lys-Gln-Arg-Phe-Arg-His-Arg-Asn-Arg-Lys-Gly-Tyr-Arg-Ser-Gln-Arg-Gly-His-Ser-Arg-Gly-Arg (8–30 of SEQ ID NO:1), or a salt, functional derivative or analog thereof, said analog being obtained by one or more amino acid substitutions, additions or deletions such that the overall properties of the analog are conserved with regard to the overall positive charge density and overall hydrophilic character of the peptide.

12. A method in accordance with claim 11, wherein said animal in need of increased fibrinolysis is a human having acute myocardial infarction, deep vein thrombosis, pulmonary embolism or disseminated intravascular coagulation.

13. A method in accordance with claim 11, wherein said molecule is BP5, BP6, BP7, BP8 or BP14.

14. A molecule capable of enhancing a biological activity of plasminogen activator inhibitor-1 (PAI-1), consisting of a peptide having 7 to 19 consecutive amino acids of the sequence:

Ser-Gln-Arg-Gly-His-Ser-Arg-Gly-Arg-Asn-Gln-Asn-Ser-Arg-Arg-Pro-Ser-Arg-Ala (22–40 of SEQ ID NO:1), or a salt, functional derivative or analog thereof, said analog being obtained by one or more amino acid substitutions, additions or deletions such that the overall properties of the analog are conserved with regard to the overall positive charge density and overall hydrophilic character of the peptide, wherein said molecule of the peptide does not include the peptide of residues 26–39 of SEQ ID NO:1.

15. A molecule according to claim 14, wherein said amino acid sequence consists of residues 22–40 of SEQ ID NO:1.

16. A molecule according to claim 14, wherein said amino acid sequence consists of residues 22–30 of SEQ ID NO:1.

17. A peptide according to claim 14, wherein all amino acid residues have the L configuration.

18. An antifibrinolytic pharmaceutical composition comprising an effective amount of a molecule in accordance with claim 14 and a pharmaceutically acceptable carrier.

19. A method for the treatment of disorders associated with excessive fibrinolysis, comprising administering an effective amount of a molecule capable of enhancing a biological activity of plasminogen activator inhibitor-1 (PAI-1), consisting of a peptide having 7 to 19 consecutive amino acids of the sequence:

Ser-Gln-Arg-Gly-His-Ser-Arg-Gly-Arg-Asn-Gln-Asn-Ser-Arg-Arg-Pro-Ser-Arg-Ala (22–40 of SEQ ID NO:1), or a salt, functional derivative or analog thereof, said analog being obtained by one or more amino acid substitutions, additions or deletions such that the overall properties of the analog are conserved with regard to the overall positive charge density and overall hydrophilic character of the peptide.

* * * * *